United States Patent [19]

Beck et al.

[11] Patent Number: 5,068,343

[45] Date of Patent: Nov. 26, 1991

[54] 4-SUBSTITUTED 5-CHLORO-2-HYDRAZINOTHIAZOLES

[75] Inventors: Gunter Beck, Leverkusen; Ernst Kysela, Bergisch Gladbach; Rudolf Braden, Odenthal, all of Fed. Rep. of Germany

[73] Assignee: Bayer Aktiengesellschaft, Leverkusen, Fed. Rep. of Germany

[21] Appl. No.: 606,375

[22] Filed: Oct. 31, 1990

[30] Foreign Application Priority Data

Dec. 9, 1989 [DE] Fed. Rep. of Germany ....... 3940794

[51] Int. Cl.$^5$ ............................................. C07D 277/50
[52] U.S. Cl. .................................. 548/194; 548/198; 548/202; 548/204
[58] Field of Search ................................ 548/194, 198

[56] References Cited

FOREIGN PATENT DOCUMENTS 3821598 12/1989 Fed. Rep. of Germany ...... 548/202

Primary Examiner—Robert Gerstl
Attorney, Agent, or Firm—Sprung Horn Kramer & Woods

[57] ABSTRACT

4-Substituted 5-chloro-2-hydrazinothiazoles of the formula

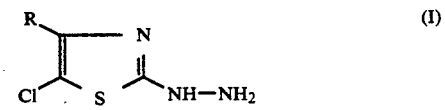

in which
R represents $CHF_2$, $CF_3$, CN or $COOR^1$, where $R^1$ represents $C_1$-$C_4$-alkyl.

They are useful as pesticides and as intermediates for other pesticides.

5 Claims, No Drawings

4-SUBSTITUTED 5-CHLORO-2-HYDRAZINOTHIAZOLES

The invention relates to new 4-substituted 5-chloro-2-hydrazinothiazoles and to intermediates, some of which are new, for their preparation.

New 5-chloro-2-hydrazinothiazoles, substituted in the 4-position, of the general formula (I)

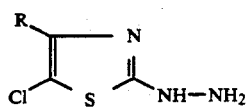

have now been found in which
R represents $CHF_2$, $CF_3$, CN or $COOR^1$,
where
$R^1$ represents $C_1-C_4$-alkyl.

The preparation of the new 5-chloro-2-hydrazinothiazoles (I)—according to processes which are known per se—is shown by the following reaction scheme:

tion scheme are to be inferred from the following examples.

Chlorination of (II) up to a final temperature of about 160° C. leads to 2,5-dichloro-4-trichloromethylthiazole (still unknown from the literature) of the formula (IV). This compound is the subject of an older previously unpublished German patent application (P 38 21 598.5 of June 27, 1988).

The compounds of the formulae (V), (VI), (VII) and (XI) which can be obtained from (IV) are also still unknown from the literature; they are also a subject of the abovementioned older German application P 38 21 598.5.

The carboxylic acid of the formula (V) is obtained from the trichloromethyl compound (IV) by reaction with water at temperatures between 80° C. and 100° C.

The carbonyl chloride of the formula (VI) is obtained from the carboxylic acid (V) by reaction with a chlorinating agent, such as, for example, thionyl chloride, at temperatures between 20° C. and 80° C.

The carboxamide of the formula (VII) is obtained from the carbonyl chloride (VI) by reaction with am-

Reaction scheme:

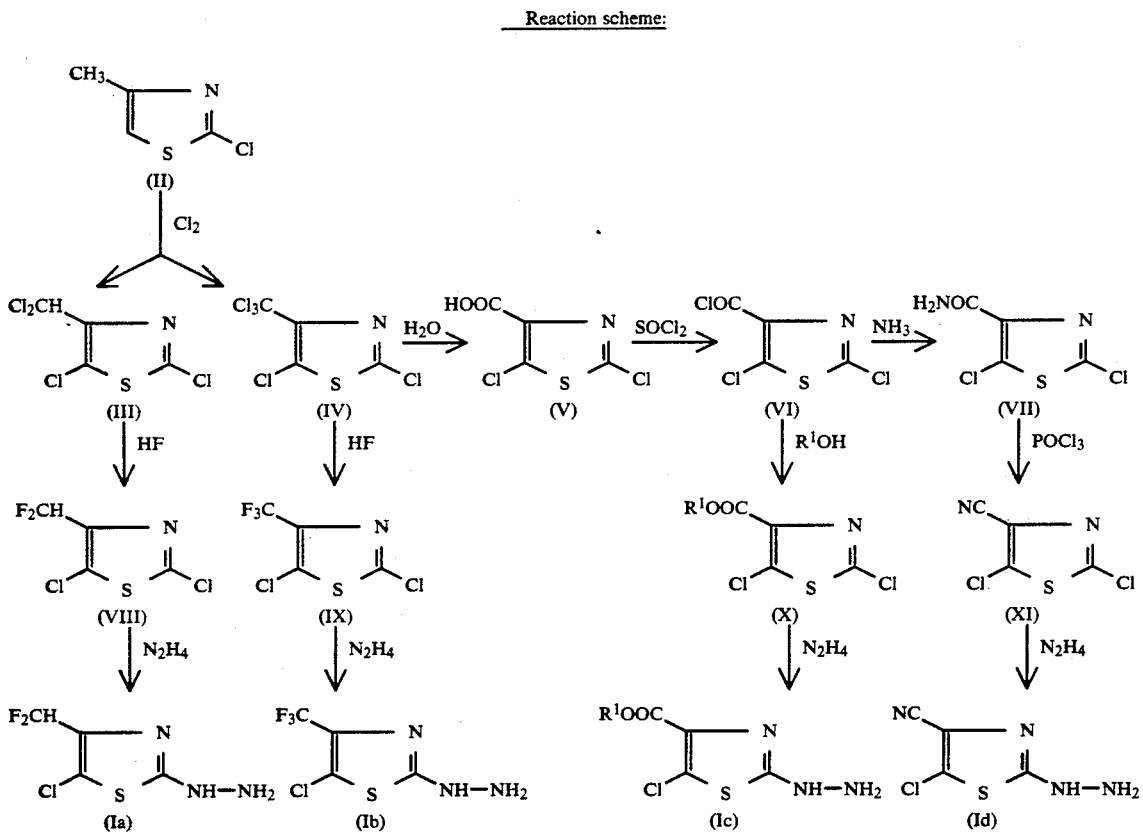

The starting compound for all 4-substituted 5-chloro-2-hydrazinothiazoles (I) is the known 2-chloro-4-methylthiazole of the formula (II) (compare J. Chem. Soc. 1919, pp. 1071-1090).

Chlorination of (II) at a temperature of about 100° C. leads predominantly to 2,5-dichloro-4-dichloromethylthiazole (still unknown from the literature) of the formula (III), which is likewise a subject of the present invention.

Preparative details of this chlorination reaction and all other reactions described in the context of the reacmonia ($NH_3$) in the presence of an inert diluent, such as, for example, toluene, at temperatures between 0° C. and 40° C.

The carbonitrile of the formula (XI) is obtained from the carboxamide (VII) by reaction with a dehydrating agent, such as, for example, phosphorus oxychloride ($POCl_3$), at temperatures between 50° C. and 150° C.

2,5-Dichloro-4-difluoromethyl-thiazole of the formula (VIII) is mentioned in an older previously unpublished German patent application (P 38 21 600.0 of June 27, 1988, corresponding to U.S. Pat. application Ser. No. 366,577 filed June 15, 1989). It is prepared by reaction of the dichloromethyl compound (III) with anhydrous hydrofluoric acid (HF), if desired under pressure, at temperatures between 40° C. and 200° C.

2,5-Dichloro-4-trifluoromethyl-thiazole of the formula (IX) is still unknown from the literature and is also a subject of the present invention. It is prepared by reaction of the trichloromethyl compound (IV) with anhydrous hydrofluoric acid, if desired under pressure, at temperatures between 40° C. and 200° C.

The 2,5-dichloro-4-thiazole-carboxylates of the formula (X) are likewise still not known from the literature and are also a subject of the present invention. They are prepared by reaction of the acid chloride of the formula (VI) with lower ($C_1$-$C_4$) aliphatic alcohols, expediently at the boiling point of the respective alcohol.

An alternative route for the preparation of the 2,5-dichloro-4-thiazolecarboxylates of the formula (X) consists in reacting the trichloromethyl compound (IV) with the lower aliphatic alcohol concerned at the boiling point and in the presence of catalytic amounts (about 1% by weight) of anhydrous iron(III) chloride.

The new 4-substituted 5-chloro-2-hydrazinothiazoles (Ia) to (Id) according to the invention are prepared in a manner known per se by reacting the corresponding 2-chlorothiazoles (VIII), (IX), (X) and (XI) (compare reaction scheme) with hydrazine (hydrate) in a suitable organic solvent, such as, for example, $C_1$-$C_3$-alcohols or (cyclic) ethers such as dioxane, at temperatures between 0° C. and 40° C.

The 4-substituted 5-chloro-2-hydrazinothiazoles of the formula (I) according to the invention possess fungicidal activity, in particular against Pyricularia oryzae on rice, Venturia inaequalis (for example on fruit), Phytophthora infestans (for example on tomatoes), Plasmopara viticola on vines and Pellicularia sasakii on rice.

Moreover, the thiazoles (I) can also be employed as intermediates for the preparation of certain azo dyestuffs, which are obtainable by oxidative coupling with appropriate anilines. The resulting 4-aminophenylazothiazoles can be used for dyeing and printing fiber materials and also for sublimation transfer printing (compare DE-A-3,804,814).

The new 4-substituted 2,5-dichlorothiazoles of the formulae (III), (IX) and (X) required as intermediates can also be mutually defined by the formula (XII):

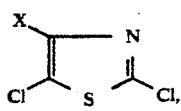

in which
X represents $CHCl_2$, $CF_3$ or $COOR^1$,
where
$R^1$ represents $C_1$-$C_4$-alkyl.

The intermediates of the formula (XII) are also a subject of the invention.

The compounds of the formula (XII) can additionally also be used as intermediates for the preparation of herbicidal thiazolyloxyacetamides (compare, for example, EP-A-18,497, US-A-4,645,525, EP-A-195,237 and US-A-4,788,291).

Moreover, the compounds of the formulae (IX) and (X) also possess fungicidal activity, in particular against Plasmopara viticola, Phytophthora infestans, Pyricularia oryzae and Venturia inaequalis.

The following Examples serve to illustrate the invention further.

PREPARATION EXAMPLES

EXAMPLE 1

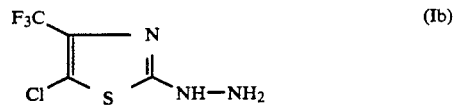

75 g (1.5 mol) of hydrazine hydrate were added to a mixture of 111 g (0.5 mol) of 2,5-dichloro-4-trifluoromethyl-thiazole (IX) and 500 ml of dioxane with stirring and gentle cooling at a rate such that a reaction temperature of 25° C. was not exceeded. After subsequently stirring at room temperature for 20 hours, the reaction mixture was stirred into 2.5 l of ice-water, then the precipitate was filtered off, and the filter residue was washed with water and dried.

87.3 g (80.3 % of theory) of 5-chloro-2-hydrazino-4-trifluoromethyl-thiazole of melting point 136°-137° C. were obtained.

EXAMPLE 2

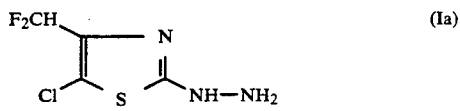

Analogously to 5-chloro-2-hydrazino-4-trifluoromethyl-thiazole (Ib), 5-chloro-4-difluoromethyl-2-hydrazinothiazole (Ia) was obtained in 51.3% yield from 2,5-dichloro-4-difluoromethyl-thiazole (VIII). Melting point 132° C. (dec.) (after recrystallizing from a large amount of cyclohexane).

Relatively small amounts of the compound (Ia) can be sublimed at as little as 70° C./0.1 mbar.

EXAMPLE 3

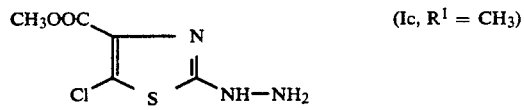

14.5 g (0.29 mol) of hydrazine hydrate were added to a mixture of 30.3 g (0.143 mol) of methyl 2,5-dichloro-4-thiazolecarboxylate (X, $R^1$=$CH_3$) and 150 g of dioxane and the reaction mixture was stirred vigorously at room temperature for three hours. It was then stirred in 1.5 l of water, and the precipitate was filtered off, washed with water and dried. Yield 6.5 g (21.9% of theory) of methyl 5-chloro-2-hydrazino-4-thiazolecarboxylate of melting point 196.5° C. (dec.).

EXAMPLE 4

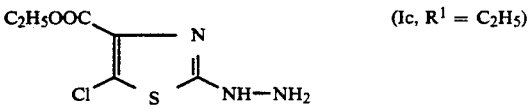

0 26.5 g (0.53 mol) of hydrazine hydrate were added at room temperature with stirring to a mixture of 40.0 g (0.177 mol) of ethyl 2,5-dichloro-4-thiazolecarboxylate (X, $R^1$=$C_2H_5$) and 175 g of dioxane. After further stirring at room temperature for 20 hours, the mixture was stirred in 1250 ml of ice-water, and the precipitate was filtered off, washed with water and dried. Yield 13.9 g (35.5% of theory) of ethyl 5-chloro-2-hydrazino-4-thiazolecarboxylate of melting point 190° C. (dec.).

EXAMPLE 5

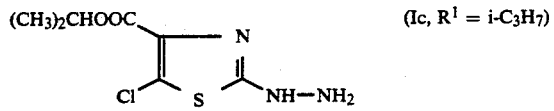
(Ic, $R^1 = i\text{-}C_3H_7$)

10.0 g (0.2 mol) of hydrazine hydrate were added with stirring to a solution of 24.0 g (0.1 mol) of isopropyl 2,5-dichloro-4-thiazolecarboxylate (X, $R^1=i\text{---}C_3H_7$) in 100 g of dioxane. After further stirring at room temperature for 15 hours, the mixture was stirred in about 500 ml of water, and the precipitate was filtered off, washed with water and dried. Yield 11.8 g (50.1% of theory) of isopropyl 5-chloro-2-hydrazino-4-thiazolecarboxylate of melting point 156°–157° C. (dec.).

EXAMPLE 6

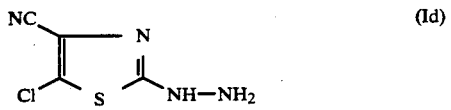
(Id)

A mixture of 10 g (0.2 mol) of hydrazine hydrate and 50 ml of methanol was added to a solution of 17.9 g (0.1 mol) of 4-cyano-2,5-dichlorothiazole (XI) in 100 ml of methanol. After about 5 minutes, a precipitate began to deposit from the slightly warmed reaction solution. After stirring overnight, the mixture was stirred in about 750 ml of water, and the precipitate was filtered off, washed with water and dried. Yield 15.2 g (87.1% of theory) of 5-chloro-4-cyano-2-hydrazino-thiazole; melting point 225° C. (dec.) (recrystallized from toluene).

EXAMPLE 7

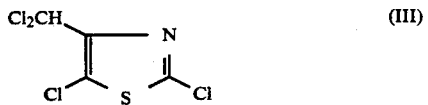
(III)

A vigorous stream of chlorine was passed initially at 80° C. and, after the exothermic reaction had subsided, at 100° C. into 5888 g (42.9 mol) of 97.3% pure 2-chloro-4-methyl-thiazole (II) for about 100 hours. After cooling to room temperature and standing overnight, a crystalline precipitate of 2,5-dichloro-4-dichloromethylthiazole (III) was formed, which was filtered off and dried on clay. Yield 3907 g (38.4% of theory).

The liquid portion of the chlorination mixture was fractionally distilled in a 2 m packed column. The distillate obtained at 101° C. to 103° C./6 mbar largely crystallized out and was then dried on clay. Yield of 2,5-dichloro-4-dichloromethylthiazole (III) by fractional distillation: 2733 g (26.9% of theory).

Total yield 6640 g (65.3% of theory). Melting point 42° C.–44° C. (recrystallized from a little petroleum ether). $^1$H-NMR (in $CDCl_3$): $\delta=6.78$ ppm.

EXAMPLE 8

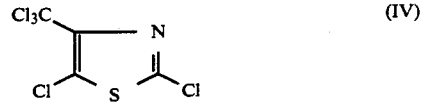
(IV)

Starting at room temperature, chlorine gas was passed into a mixture of 1093 g (8.19 mol) of 2-chloro-4-methyl-thiazole and 4 l of methylene chloride in a 3-necked flask which was provided with a stirrer, thermometer, reflux condenser and gas inlet tube. After the exothermic reaction had subsided, the methylene chloride was initially distilled off while gradually increasing the temperature and passing in further chlorine and then the bottom was slowly heated to about 160° C. At about 160° C., mostly excess chlorine gas (detectable from the slightly greenish color of the waste gas) was passed in until almost only the desired compound 2,5-dichloro-4-trichloromethyl-thiazole could be detected in the gas chromatogram. Total duration of the chlorination 40 to 50 hours.

A coarse distillation up to a head temperature of 150° C. at 14 mbar produced 2057 g of about 95% pure 2,5-dichloro-4-trichloromethyl-thiazole, which corresponds to a yield of 88% of theory, relative to pure product. The 2,5-dichloro-4-trichloromethyl-thiazole was obtained pure by precision distillation in a silvered packed column about 220 cm long. Boiling point 123° C.–125° C. at 16 mbar.

EXAMPLE 9

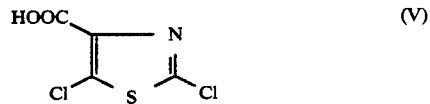
(V)

271.5 g (1 mol) of 2,5-dichloro-4-trichloromethyl-thiazole and 2700 ml of water were heated under reflux with stirring overnight (about 15 hours). After cooling to room temperature, the resulting crystalline precipitate was filtered off, washed with water and dried.

Yield 143.5 g (72.5% of theory) of 2,5-dichloro-thiazole-4-carboxylic acid. The compound can be sublimed at 120° C./0.1 mbar and can be recrystallized, for example, from chloroform. Melting point 191° C. with decomposition. It was possible to isolate a further 30.5 g of somewhat less pure product by concentrating the aqueous phase.

EXAMPLE 10

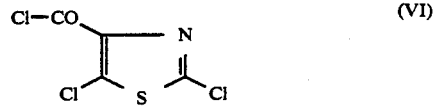
(VI)

A mixture of 143.5 g (0.725 mol) of 2,5-dichloro-thiazole-4-carboxylic acid and 700 ml of thionyl chloride were slowly heated with stirring. Vigorous evolution of gas commenced at about 40° C. The mixture was heated to reflux temperature in the course of half an hour and was kept at this temperature until the evolution of gas was complete (about 2 hours): final temperature about 80° C.

After stripping off the excess thionyl chloride in a water jet vacuum 144.6 g (92.2% of theory) of crystalline 4-chlorocarbonyl-2,5-dichloro-thiazole remained. Large colorless crystals of melting point 58° C.–59° C. from petroleum ether.

EXAMPLE 11

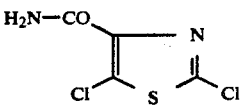 (VII)

61 g (3.59 mol) of ammonia gas was passed with stirring and cooling over a solution of 144.6 g (0.668 mol) of 4-chlorocarbonyl-2,5-dichloro-thiazole (VI) in 750 ml of anhydrous toluene at a maximum of 20° C. The resulting precipitate was then filtered off, washed with toluene, dried and stirred in 1 l of ice-water for about one hour.

After filtering off, washing with water and drying, 127.9 g (97.2% of theory) of 2,5-dichlorothiazole-4-carboxamide of melting point 153° C. were obtained.

EXAMPLE 12

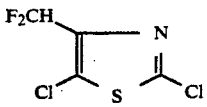 (VIII)

1010 g (4.26 mol) of 2,5-dichloro-4-dichloromethyl-thiazole (III) were fluorinated in a VA autoclave at 145° C./25 bar using 1500 ml of anhydrous hydrofluoric acid. The resulting hydrogen chloride was continuously released. After completion of the reaction, the excess hydrofluoric acid was stripped off in vacuo at room temperature. The residue was poured into ice-water, the precipitate was taken up in dichloromethane, and the solution was dried over sodium sulphate and distilled.

753 g (86.6% of theory) of 2,5-dichloro-4-difluoromethyl-thiazole (VIII), boiling point 74°–75° C./18 mbar; $n_D^{20} = 1.5171$ was obtained.

EXAMPLE 13

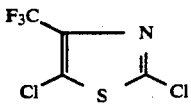 (IX)

750 g (2.76 mol) of 2,5-dichloro-4-trichloromethyl-thiazole (IV) were fluorinated in a VA autoclave at 130° C./19–20 bar using 1000 ml of anhydrous hydrofluoric acid. The resulting hydrogen chloride was continuously released. After completion of the reaction, the excess hydrofluoric acid was stripped off in vacuo at room temperature. The residue was poured into ice-water, the precipitate was taken up in dichloromethane, and the solution was dried over sodium sulphate and distilled.

570 g (93% of theory) of 2,5-dichloro-4-trifluoromethyl-thiazole were obtained; boiling point: 164° C.; $n_D^{20} = 1.4774$.

EXAMPLE 14

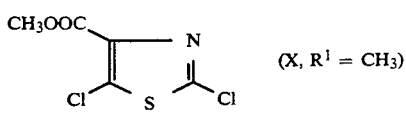 (X, $R^1 = CH_3$)

A solution of 100 g of 4-chlorocarbonyl-2,5-dichloro-thiazole (VI) in 500 ml of methanol was heated to boiling for 15 minutes. After stripping off the excess methanol at about 25° C. in vacuo, 97 g (99% of theory) of colorless oily methyl 2,5-dichloro-4-thiazolecarboxylate remained, which solidified on standing to give a white crystalline material of melting point 46° C.

EXAMPLE 15

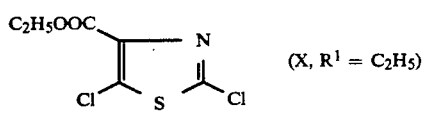 (X, $R^1 = C_2H_5$)

Ethyl 2,5-dichloro-4-thiazolecarboxylate was obtained as a colorless oil in an analogous manner to that of Example 14.

The eight strongest IR bands (in cm$^{-1}$) are: 1725, 1498, 1453, 1325, 1307, 1206, 1056 and 1020.

EXAMPLE 16

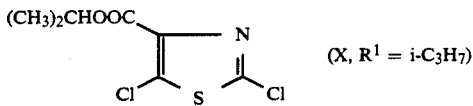 (X, $R^1 = i-C_3H_7$)

Isopropyl 2,5-dichloro-4-thiazolecarboxylate of melting point 46° C. was obtained in an analogous manner to that of Example 14.

EXAMPLE 17

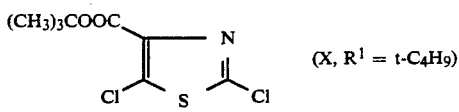 (X, $R^1 = t-C_4H_9$)

Tertiary butyl 2,5-dichloro-4-thiazolecarboxylate of melting point 190° C.–191° C. (dec.) was obtained in an analogous manner to that of Example 14.

EXAMPLE 18

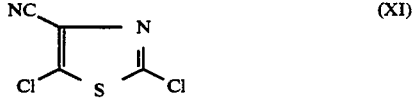 (XI)

127.8 g (0.649 mol) of 2,5-dichloro-thiazole-4-carboxamide (VII) and 1300 ml of phosphorus oxychloride were heated under reflux (about 110° C.) with stirring for about 5 hours. After distilling off the main amount of excess phosphorus oxychloride in a water jet vacuum, the oily residue was added dropwise to about 1 l of water which was kept between 15° C. and 20° C. by cooling. The crystalline precipitate resulting in this way was filtered off, washed with water and dried.

103 g (88.7% of theory) of 4-cyano-2,5-dichlorothiazole was obtained in this way. The compound can be distilled at 114° C./16 mbar, sublimed at 80° C./16 mbar and melts at 56.5° C.–57° C.

USE EXAMPLES

Example A

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

Active compounds, concentrations and test results can be seen from the following Table A.

TABLE A

| Pyricularia test (rice)/protective | |
|---|---|
| Active compound (Example No.) | Degree of action in % of the untreated control at an active compound concentration of 250 ppm |
| F$_3$C–C(Cl)=C–N=C(NH–NH$_2$)–S (1) | 100 |
| C$_2$H$_5$OOC–C(Cl)=C–N=C(NH–NH$_2$)–S (4) | 89 |
| (CH$_3$)$_2$CHOOC–C(Cl)=C–N=C(Cl)–S (16) | 80 |
| (CH$_3$)$_3$COOC–C(Cl)=C–N=C(Cl)–S (17) | 90 |

Example B

Venturia test (apple)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

Active compounds, concentrations and test results can be seen from the following Table B.

TABLE B

| Venturia test (apple)/protective | |
|---|---|
| Active compound (Example No.) | Degree of action in % of the untreated control at an active compound concentration of 250 ppm |
| C$_2$H$_5$OOC–C(Cl)=C–N=C(NH–NH$_2$)–S (4) | 67 |
| (CH$_3$)$_2$CHOOC–C(Cl)=C–N=C(NH–NH$_2$)–S (5) | 80 |
| F$_3$C–C(Cl)=C–N=C(Cl)–S (13) | 100 |
| (CH$_3$)$_2$CHOOC–C(Cl)=C–N=C(Cl)–S (16) | 70 |
| (CH$_3$)$_3$COOC–C(Cl)=C–N=C(Cl)–S (17) | 50 |

Example C

Phytophthora test (tomato)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and about 20° C.

Evaluation is carried out 3 days after the inoculation.

Active compounds, concentrations and test results can be seen from the following Table C.

TABLE C

Phytophthora test (tomato)/protective

| Active compound (Example No.) | Degree of action in % of the untreated control at an active compound concentration of 250 ppm |
|---|---|
| F₂CH—C(Cl)=C—N=C(S)—NH—NH₂ (2) | 50 |
| (CH₃)₂CHOOC—C(Cl)=C—N=C(S)—NH—NH₂ (5) | 67 |
| NC—C(Cl)=C—N=C(S)—NH—NH₂ (6) | 72 |
| F₃C—C(Cl)=C—N=C(S)—Cl (13) | 67 |

Example D

Plasmopara test (vines)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100 % relative atmospheric humidity for 1 day. The plants are then placed in a greenhouse at 22° C. and about 80 % atmospheric humidity for 5 days. The plants are then moistened and placed in a humidity chamber for 1 day.

Evaluation is carried out 7 days after the inoculation.

Active compounds, concentrations and test results can be seen from the following Table D.

TABLE D

Plasmopara test (vines)/protective

| Active compound (Example No.) | Degree of action in % of the untreated control at an active compound concentration of 10 ppm |
|---|---|
| C₂H₅OOC—C(Cl)=C—N=C(S)—NH—NH₂ (4) | 60 |
| (CH₃)₂CHOOC—C(Cl)=C—N=C(S)—Cl (16) | 90 |

EXAMPLE E

Pellicularia test (rice)
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

Active compound, concentrations and test results can be seen from the following Table E.

TABLE E

Pellicularia test (rice)

| Active compound (Example No.) | Active compound concentration | Degree of action in % of the untreated control |
|---|---|---|
| CH₃OOC—C(Cl)=C—N=C(S)—NH—NH₂ (3) | 250 ppm | 80 |
|  | 50 ppm | 70 |

It will be understood that the specification and examples are illustrative but not limitative of the present invention and that other embodiments within the spirit and scope of the invention will suggest themselves to those skilled in the art.

We claim:

1. A 4-substituted 5-chloro-2-hydrazinothiazole of the formula

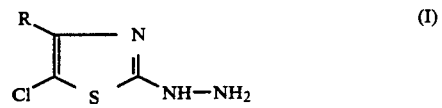

(I)

in which
R represents CHF₂, CF₃, CN or COOR¹, where
R¹ represents C₁-C₄-alkyl.

2. A compound according to claim 1 of the formula

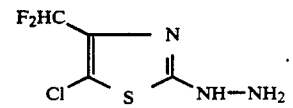

3. A compound according to claim 1 of the formula

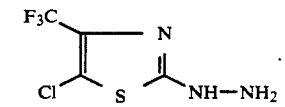

4. A compound according to claim 1 of the formula

5. A compound according to claim 1 of the formula
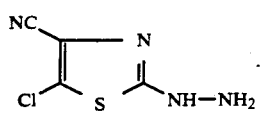
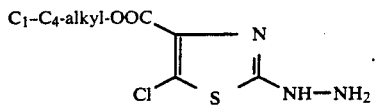
* * * * *